United States Patent [19]

Winkler

[11] Patent Number: 5,275,605
[45] Date of Patent: Jan. 4, 1994

[54] APPARATUS FOR REMOVING CALCULI FROM ANIMAL BODIES

[76] Inventor: Klaus Winkler, Edinghäuser Str. 16, D-4500 Osnabrück, Fed. Rep. of Germany

[21] Appl. No.: 993,301

[22] Filed: Dec. 18, 1992

[30] Foreign Application Priority Data

Jan. 8, 1992 [DE] Fed. Rep. of Germany ....... 4200258

[51] Int. Cl.⁵ .............................................. A61B 17/22
[52] U.S. Cl. ...................................... 606/128; 606/1; 606/108; 606/127; 604/97; 604/99
[58] Field of Search ................................. 128/765-769, 128/749, 750; 604/19, 27, 35-39, 43, 80, 93, 96, 97, 99, 128, 131, 149, 151, 181, 187; 606/1, 108, 127, 128

[56] References Cited

U.S. PATENT DOCUMENTS

| | | | |
|---|---|---|---|
| 3,316,910 | 5/1967 | Davis | 606/127 |
| 4,243,040 | 1/1981 | Beecher | 606/127 |
| 4,560,378 | 12/1985 | Weiland | 604/181 |
| 4,611,594 | 9/1986 | Grayhack et al. | 606/127 |
| 4,997,435 | 3/1991 | Demeter | 606/127 |

FOREIGN PATENT DOCUMENTS

| | | |
|---|---|---|
| 2057636 | 3/1972 | Fed. Rep. of Germany . |
| 2104673 | 5/1972 | Fed. Rep. of Germany . |
| 3616205 | 11/1987 | Fed. Rep. of Germany . |
| 3902943 | 8/1990 | Fed. Rep. of Germany . |
| 9101684 | 6/1991 | Fed. Rep. of Germany . |

*Primary Examiner*—Stephen C. Pellegrino
*Assistant Examiner*—Glenn K. Dawson
*Attorney, Agent, or Firm*—Darby & Darby

[57] ABSTRACT

Apparatus for removing kidney stones or other calculi from the cavities of animal bodies by litholysis has an expandible and collapsible receptacle of acid-resistant material and a mechanism for introducing the receptacle into a cavity so that an inlet of the receptacle admits the calculus to be removed. A closure is thereupon actuated from the outside of the animal body to seal the inlet prior to circulation of an acid solvent through the thus sealed receptacle. The acid dissolves the calculus, and the dissolved calculus is evacuated from the receptacle with the solvent. The receptacle is thereupon flushed (if necessary) and collapsed to facilitate its extraction from the cavity. The circulating system can employ a solvent-admitting first conduit, a solvent evacuating second conduit, and discrete pumps one of which admits fresh solvent into the first conduit and the other of which draws solvent and dissolved calculus from the second conduit. A single conduit can be used for alternating admission of fresh solvent into and evacuation of solvent and dissolved calculus from the receptacle. It is also possible to employ a solvent-containing bottle which is connected to the first conduit and is located at a first level, and a second bottle which is located at a second level below the first level and is connected with the second conduit to receive solvent and dissolved calculus.

17 Claims, 2 Drawing Sheets

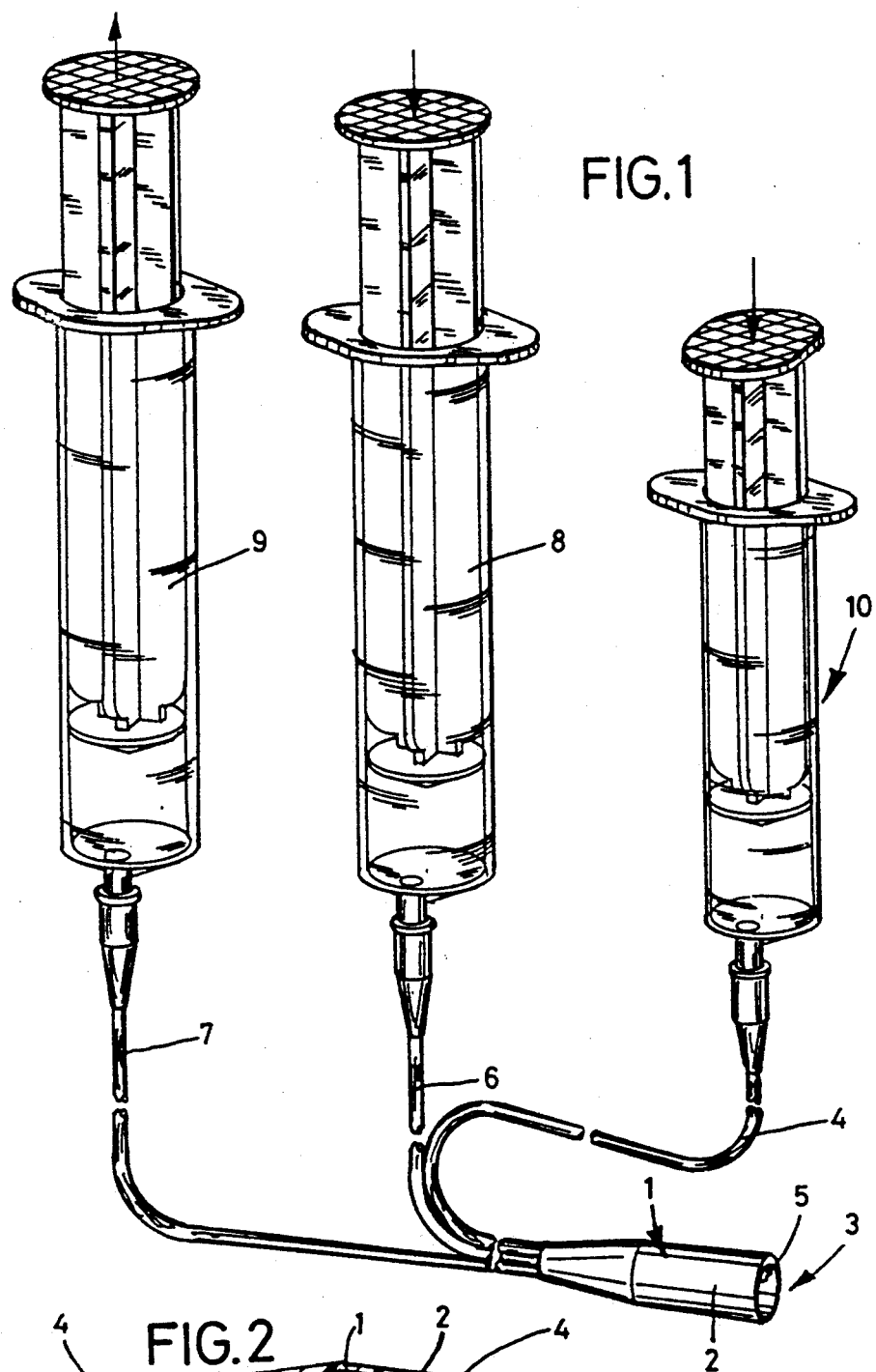
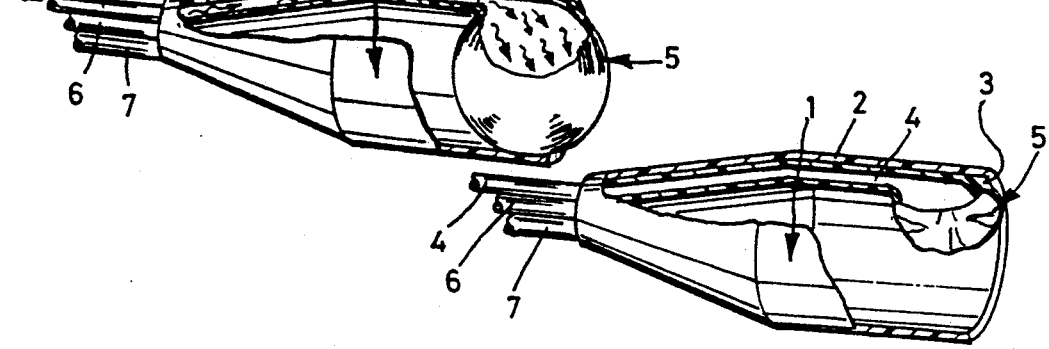

APPARATUS FOR REMOVING CALCULI FROM ANIMAL BODIES

BACKGROUND OF THE INVENTION

The invention relates to improvements in apparatus for removing calculi (such as gall stones, urinary calculi or renal calculi) from cavities of animal bodies, particularly human bodies. More particularly, the invention relates to improvements in apparatus for dissolving calculi in animal bodies prior to evacuation of dissolved calculi through an ureter, through the urethra or through another passage leading to or constituting a body cavity.

It is known to employ a cystoscope for introduction into an ureter of an apparatus for withdrawal of renal calculi. Such apparatus employ one or more loops or a spreadable element which must be applied around a calculus in the ureter. The spreadable element or the loops are thereupon weighted and/or otherwise pulled to gradually draw the renal calculus into the urinary bladder. A drawback of these apparatus is that their spreadable element and/or loops cannot properly engage all kinds of calculi, e.g., renal calculi which exhibit sharp edges and are firmly anchored in the ureter. Furthermore, even if the calculus is adequately engaged by one or more loops and/or by another suitable (e.g., spreadable) element, it is likely to cause injury to tissue around the ureter during extraction from the ureter into the urinary bladder. The tissue surrounding a renal calculus is also likely to be damaged during application of one or more loops and/or other engaging elements around a calculus which is rather firmly anchored in the ureter.

German patent application Serial No. 20 57 636 of Rudolf Necke (published Mar. 9, 1972) discloses an apparatus which is designed to evacuate concretions in a manner causing less trauma to the patient. The patented apparatus employs a twin-walled hose having a twin-walled inlet in the form of a calyx. The inlet is surrounded and maintained in collapsed condition by a sheath which is operative during introduction of the hose and inlet into an ureter close to a calculus but is thereafter withdrawn or retracted prior to admission of a gaseous or liquid medium between the walls of the thus exposed hose and between the walls of its inlet. The thus expanded inlet is then ready to guide the calculus into the hose during further introduction of the patented apparatus into the ureter. The configuration of the aforediscussed sheath is such that its front side is rounded while it confines and maintains the inlet of the hose in the collapsed condition. This reduces the likelihood of injury and of pronounced trauma during introduction of the apparatus into a body cavity adjacent to a calculus. The sheath can maintain the inlet in collapsed condition by folding or in a similar way. A cystoscope is utilized to introduce the apparatus into the ureter, and the introduction is monitored by the person or persons in charge to ensure that the forward progress of the hose is interrupted and the inlet is expanded shortly before the apparatus reaches the calculus. Expansion of the inlet is intended to ensure gradual and rather gentle expansion of the ureter with attendant loosening of the calculus which is then caused to enter the hose through the expanded inlet. The fluid pressure between the walls of the hose as well as between the walls of the inlet is thereupon reduced to cause gradual collapse of such parts and gradual narrowing (contraction) of the ureter. The collapsed inlet surrounds at least the major portion of the entrapped calculus during ensuing extraction from the cavity.

German patent application Serial No. 39 02 943 of Ulrich Leuschner et al. (published Aug. 9, 1990) discloses an apparatus which introduces a liquid solvent into a body cavity, especially into a gallbladder. The apparatus is further designed to evacuate by suction a mixture consisting of solvent, sludge of dissolved calculus and secretions of the gall. The evacuating means comprises a piston pump. Provisions are made to segregate the solvent from secretions by resorting to a suitable separator. A drawback of this patented apparatus is that, in contrast to the operation of the previously described apparatus employing a hose with a calyx-shaped inlet for a calculus, dissolution of the calculus in the interior of an animal body involves direct contact between the solvent and the body tissue. This can cause extensive damage to the tissue and/or to one or more organs.

The situation is similar in connection with apparatus which is disclosed in German patent application Serial No. 36 16 205 of Ulrich Leuschner (published Nov. 19, 1987). This patent discloses a twin-balloon catheter for selective admission of liquids into the gallbladder. The catheter is fixed in the bile duct and the latter is then sealed from above (i.e., from the liver) and from below (i.e., from the intestine). One of the balloons seals from the liver and the other balloon seals from the intestine. An opening between the two balloons then admits a suitable medium into the bile duct.

German Utility Model No. G 91 01 684 (owned by Andrea Scarfi and published Jun. 20, 1991) discloses a sac for extraction of substances from the stomach. This publication does not deal with the dissolution of calculi.

German patent application Serial No. 21 04 673 of Rudolf Necke (published May 31, 1972) discloses an apparatus for removal of urinary calculi and of calculi which are lodged in the lower part of the pelvis of a kidney. The apparatus employs an expandible calyx which can be introduced into the urinary tract to expand the urinary tract and to thus facilitate introduction of the calculus into the calyx. Once the calculus is confined in the calyx, the latter is caused to contract and to thus capture the calculus for extraction (in undissolved condition) from the body of a patient.

OBJECTS OF THE INVENTION

An object of the invention is to provide a novel and improved apparatus for removal of calculi from animal bodies which is safer and whose utilization is less traumatic to patients than heretofore known apparatus.

Another object of the invention is to provide a novel and improved apparatus for dissolving calculi in animal bodies.

A further object of the invention is to provide an apparatus for non-operative removal of calculi from body cavities.

An additional object of the invention is to provide the apparatus with novel and improved means for shielding tissue from damage by substances which are sufficiently potent to dissolve calculi in animal bodies.

Still another object of the invention is to provide the above outlined apparatus with novel and improved means for introducing a solvent into and for evacuating a solvent from animal bodies.

A further object of the invention is to provide an apparatus which need not appreciably expand the passages leading to calculi in ureters, in urethrae and/or in other parts of body cavities.

Another object of the invention is to provide the apparatus with novel and improved means for receiving a calculus within the confines of an animal body.

An additional object of the invention is to provide the apparatus with novel and improved means for facilitating confinement of a calculus prior to removal from a body cavity.

Still another object of the invention is to provide a novel and improved litholysis method of evacuating calculi from urethrae, ureters, urinary bladders and/or other cavities in animal bodies.

A further object of the invention is to provide a novel method of evacuating a calculus in the course of its dissolution in an animal body.

Another object of the invention is to provide a novel and improved method of sealing a confined calculus from tissue in an animal body.

An additional object of the invention is to provide a simple and inexpensive apparatus for the practice of the above outlined method.

SUMMARY OF THE INVENTION

The invention is embodied in an apparatus for removing acid-soluble calculi (e.g., kidney stones) from cavities of animal bodies. The improved apparatus comprises an acid-resistant receptacle having an inlet for admission of a calculus, means for introducing the receptacle into a calculus-containing cavity to thus admit a calculus into the introduced receptacle through the inlet, means for sealing the inlet upon admission of a calculus into the introduced receptacle, means for actuating the sealing means from the outside of the cavity, and means for circulating an acid solvent through the receptacle (while the inlet is sealed and a calculus is confined in the receptacle) to thus dissolve the confined calculus and to flush the dissolved calculus from the receptacle.

The receptacle can comprise a collapsible and expandible sac.

The circulating means can comprise means for admitting acid solvent into the receptacle from the exterior of the cavity and means for evacuating acid solvent and dissolved calculus from the receptacle to the exterior of the cavity. The admitting means can comprise a first conduit and the circulating means can further comprise means for forcing acid solvent into the conduit at the exterior of the cavity. The evacuating means of such apparatus can comprise a second conduit and the circulating means can further comprise means for receiving liquid solvent and dissolved calculus from the receptacle at the exterior of the cavity. At least one of the forcing and receiving means can comprise a pump, e.g., a syringe. Alternatively, the forcing means can comprise a solvent-containing first vessel which is disposed at a first level, and the receiving means can comprise a second vessel disposed at a second level below the first level.

The sealing means can comprise an inflatable and deflatable closure for the inlet. The actuating means then comprises means for inflating such closure. The inflating means can comprise a conduit which is connected with the closure and extends from the cavity upon introduction of the receptacle, and means for forcing a fluid into the closure through the conduit from the exterior of the cavity.

As mentioned above, the receptacle can constitute an expandible and collapsible sac or is otherwise deformable to facilitate its introduction into and/or its withdrawal from a body cavity. Such apparatus can further comprise means for deforming the receptacle from the exterior of a cavity upon introduction of the receptacle into such cavity. The configuration of the receptacle can be such (e.g., the receptacle can resemble a tube) that it has a variable diameter.

Collapsibility of the receptacle facilitates introduction of such receptacle into and its withdrawal, from a body cavity.

The circulating means can comprise at least one conduit extending from the introduced receptacle to the exterior of the cavity and at least one pump which is connectable with the at least one conduit at the exterior of the cavity which receives the receptacle. For example, the apparatus can be furnished with a first syringe which supplies solvent into the at least one conduit and with a second syringe which serves to withdraw the solvent and dissolved calculus from the receptacle.

The conduit or conduits of the circulating means can form part of a cable to facilitate introduction of the receptacle into a cavity. Alternatively, at least one of the conduits forming part of the circulating means can form a cable with one or more conduits of the means for actuating the sealing means. Still further, one or more conduits of the circulating means, one or more conduits of the actuating means and/or one or more conduits of the means for expanding and collapsing the receptacle, can be combined into a single cable to facilitate introduction of the receptacle into and its withdrawal from a body cavity, e.g., through the urethra and the urinary bladder and thereupon into an ureter to a position for reception of a kidney stone.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawings.

BRIEF DESCRIPTION OF THE DRAWINGS

FIG. 1 is a fragmentary perspective view of an apparatus which embodies one form of the invention and employs discrete pumps for admission of solvent into and for evacuation of solvent and dissolved calculi from the receptacle;

FIG. 2 is an enlarged perspective view of the receptacle, with the closure for the inlet of the receptacle shown in sealing position, a portion of the receptacle and of the closure being broken away;

DESCRIPTION OF PREFERRED EMBODIMENTS

Figure 3:
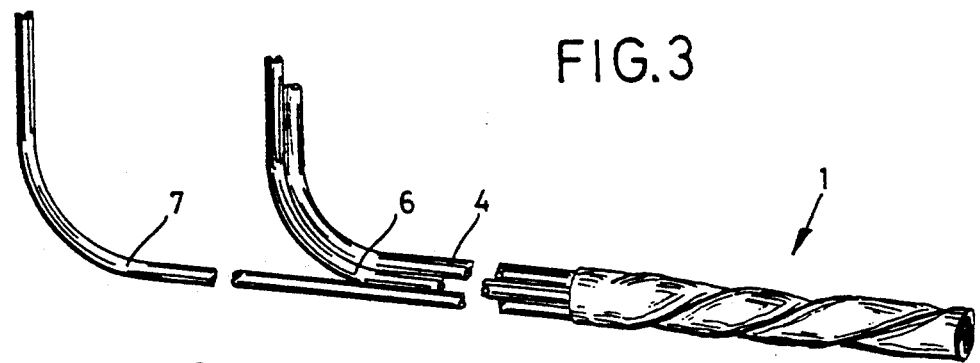
FIG. 3 is a fragmentary perspective view of a modified apparatus with a twistable receptacle.

Referring first to FIG. 1, there is shown an apparatus which comprises a receptacle in the form of a sac 1 made of caoutchouc or another suitable acid-resistant material. The dimensions of the receptacle 1 are selected in such a way (or the receptacle can be collapsed to such an extent) that it can be readily introduced into a body cavity, for example, through the urethra and through the urinary bladder into one of the ureters and, if necessary, all the way to or into the pelvis of a kidney. Once introduced sufficiently close to a confined calculus (such as a renal calculus), the receptacle is expanded (if necessary) to receive and confine the calculus. A wall 2 of the receptacle 1 carries a deformable sealing element or closure 5 which can be inflated and/or otherwise manipulated to seal an inlet 3 of the receptacle as soon as the latter properly receives and confines a calculus. Thus, the internal space of the receptacle 1 is then sealed from the kidney, from the respective ureter and from all surrounding tissue. The means for actuating the closure 5 to cause the latter to assume the closing or sealing position of FIG. 2 includes a conduit 4 which extends from the proximal end of the receptacle 1 to the exterior of the body of a patient and is connected with or is connectable to a small pump 10, e.g., a syringe, which can be actuated by hand or otherwise to seal the inlet 3 of the receptacle 1 by inflating and/or otherwise influencing the closure 5. The inlet 3 is sealed to such an extent that it prevents any flow, or any appreciable flow, of fluids from and/or into the internal space of the receptacle 1 by way of the inlet 3. This is important when the nature of a solvent which is used to dissolve a confined calculus is such that it could cause much damage to the tissue around the fully inserted receptacle 1 and/or to the adjacent organ.

The means for circulating an acid solvent or another suitable solvent through the receptacle 1 (while the latter contains a calculus and while its inlet 3 is sealed by the closure 5) comprises two solvent-resistant conduits 6, 7, which are connected to the proximal end of the receptacle and extend from the animal body, e.g., from the body of a human patient. The means for admitting solvent via conduit 6 comprises a first pump 8 (e.g., a syringe) which can constitute a source of solvent, and the means for evacuating solvent and dissolved calculus from the internal space of the receptacle 1 through the conduit 7 comprises a second pump 9 (e.g., a syringe). The pumps 8 and 9 are located outside of the body cavity. The conduits 4, 6 and 7 can be designed and coupled to each other in such a way that they constitute (or form part of) the means for introducing the receptacle 1 into a selected portion of a body cavity, e.g., into the pelvis of a kidney or into one of the ureters.

Figure 6:
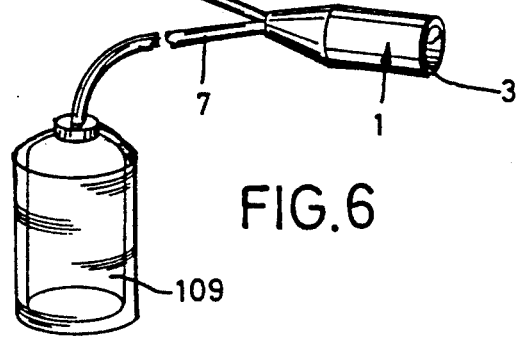
FIG. 6 is a fragmentary schematic elevational view of an apparatus wherein a first vessel serves to admit solvent into the receptacle by gravity flow and a second vessel serves to receive solvent and a dissolved calculus by gravity flow.

It is clear that the pump or syringe 8 and/or 9 can be replaced with other suitable means for respectively introducing a solvent into and for evacuating solvent and dissolved calculus from the sealed receptacle 1. For example, and as shown in FIG. 6, the pump 8 can be replaced with a first infusor vessel 108 which is disposed at a first level to admit a solvent into the conduit 6 by gravity flow, and the pump 9 can be replaced by a second vessel 109 located at a second level below the first level and serving to receive spent solvent and dissolved calculus through the conduit 7.

When the apparatus of FIG. 1 is in actual use, i.e., when a calculus is already confined in the internal space of the receptacle 1 and the inlet 3 of this receptacle is properly sealed by the closure 5, the pump 8 is actuated first to admit a selected quantity of solvent through the conduit 6. The next step involves actuation of the pump 9 in a sense to draw a mixture of spent solvent and the already dissolved portion of the calculus through the conduit 7. These procedures are thereupon repeated as often as necessary in order to complete the dissolution and evacuation of the entire calculus. The next step can involve replacement of the pump 8 or 9 with a pump which contains a supply of flushing liquid and replacement of the pump 9 or 8 with a pump which can receive spent flushing liquid. When the flushing of the interior of the receptacle 1 is completed, the receptacle is collapsed (e.g., deflated simultaneously with deactivation of the closure 5) and the receptacle, its closure and the conduits 4, 6 and 7 are then ready for withdrawal from the body of a patient.

It is clear that the circulating means with two conduits 6 and 7 constitutes but one of a variety of circulating means which can be utilized for the practice of the present invention. For example, the conduit 6 or 7 can be omitted and the apparatus then employs two pumps (e.g., the pumps 8, 9) or two vessels (e.g., 108, 109) one of which is attached to the proximal end of the conduit 6 or 7 to admit a supply of solvent and the other of which thereupon replaces the one pump or vessel to receive spent solvent and dissolved calculus. Such alternating admission of solvent into and evacuation of a mixture of solvent and dissolved calculus is repeated as often as necessary, i.e., until the evacuation of the fully dissolved calculus is completed.

It is further clear that the receptacle 1 need not be flushed prior to extraction from the body of a patient. For example, if the inlet 3 can remain sealed and the receptacle can be adequately collapsed or contracted for convenient withdrawal from a body, the flushing operation can be carried out upon extraction of the receptacle, e.g., through the urethra.

FIG. 2 shows the receptacle 1 (which resembles a relatively short hose or tube) in expanded condition. The closure 5 is shown in operative or actuated condition, i.e., it seals the inlet 3 from the surrounding area. The receptacle 1 and/or the closure 3 has twin walls to define a path for admission of a fluid from the pump 10 and through the conduit 4 in order to expand the receptacle and/or to move the closure 5 to the sealing position. Lifting of the plunger of the pump 10 will result in a collapse of the receptacle 1 and/or in retraction or collapse of the closure 5 to an inoperative position so that the inlet 3 is exposed and the receptacle is ready for extraction from the body of a patient or for reception of a calculus.

FIG. 3 shows a portion of another apparatus which employs a thin-walled receptacle 1 adapted to be twisted into a practically solid elongated flexible member ready to be introduced into a body cavity. The properly introduced twisted member 1 can be expanded to receive a calculus in response to admission of a fluid through at least one of the conduits 4, 6, 7. For example, the twisted receptacle 1 of FIG. 3 can be introduced all the way into one of the ureters or all the way into the pelvis of a kidney. By way of example only, when expanded the receptacle 1 of FIG. 3 can have a diameter of 0.8 to 1.5 cm.

Figure 4:
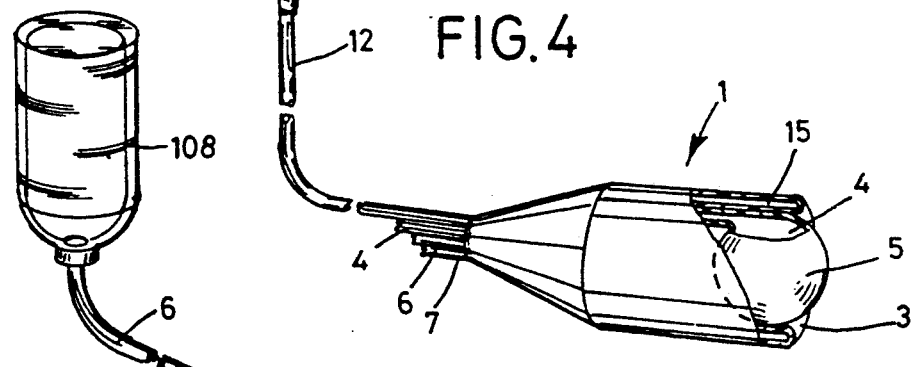
FIG. 4 is a perspective view of a portion of a further apparatus with an inflatable and deflatable receptacle.

FIG. 4 illustrates a portion of a further apparatus wherein the means for inducing expansion or collapse of an elongated tubular receptacle 1 includes a further pump 11 (e.g., a syringe) connected to the proximal end of the receptacle by a further flexible conduit 12. The receptacle 1 of FIG. 4 has a twin wall 15 which defines an annular compartment serving to receive a supply of gaseous or liquid fluid in order to expand the receptacle subsequent to introduction into close proximity of a calculus. The structure of FIG. 4 can be used to calibrate the receptacle 1, i.e., to select the diameter of the expanded receptacle for dissolution of a particular calculus. The closure or sealing element 5 is or can be designed in such a way that it automatically seals the inlet 3 in response to expansion of the receptacle 1. Alternatively, and as actually shown in FIG. 4, the sealing element 5 can be actuated by a fluid which is to be admitted through the conduit 4.

Figure 5:
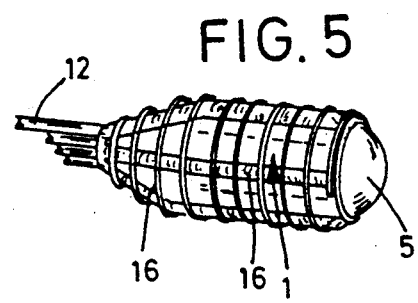
FIG. 5 is a fragmentary perspective view of a receptacle constituting a modification of the receptacle of FIG. 4.

FIG. 5 shows a further receptacle 1 which can be expanded in response to admission of a fluid medium through the conduit 12 and into a helical conduit 16 which surrounds the wall of the receptacle. Such receptacle need not have a twin wall. Furthermore, the helical conduit 16 can be replaced by or used jointly with conduits extending in substantial parallelism with the axis of the tubular receptacle 1 to ensure that the receptacle expands in response to admission of a suitable fluid through the conduit 12.

Figure 3A:
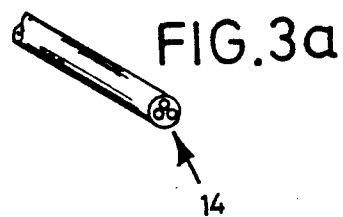
FIG. 3a is a fragmentary perspective view of a cable which unites three conduits.

FIG. 3a shows a portion of a cable 14 which replaces the conduits 4, 6 and 7 or 4, 6 and 12 or 4, 7 and 12. Furthermore, this cable can be replaced with a cable defining four passages, i.e., with a cable which can be used in lieu of conduits 4, 6, 7 and 12. An advantage of the cable 14 or an equivalent cable is that it contributes to convenience of introduction of the receptacle 1 into an animal body. For example, the diameter of the cable 14 can be in the range of 2 mm which is not much more than the diameter of the conduit 4, 6, 7 or 12.

An important advantage of the improved method and apparatus is that the removal of a calculus is nearly painless. Thus, the path to a calculus must be expanded just sufficiently to permit introduction of the collapsed receptacle 1 into close proximity to the calculus which is to be removed (dissolved). The receptacle 1 is thereupon expanded to an extent which is necessary to permit introduction of the calculus through the unsealed inlet 3, and the sealing element or closure 5 is thereupon actuated to seal the inlet. The apparatus is then ready to start with dissolution of the calculus in the internal space of the receptacle 1. Withdrawal or extraction of the apparatus is equally painless since the receptacle 1 can be collapsed to a fraction of its maximum diameter to be thereupon withdrawn from the cavity.

Another important advantage of the improved apparatus is that the solvent cannot come in contact with the tissue and/or with one or more organs. This enhances the safety of the calculus removing operation while permitting the use of a highly effective solvent which can complete the dissolution of a confined calculus within a short interval of time. All that is necessary is to make the receptacle 1, its closure 5 and the conduits 6 and 7 of a material which can stand the action of the solvent and of a mixture of solvent with dissolved calculus.

A further important advantage of the improved apparatus is that the introduction of the preferably collapsible receptacle 1 into and its extraction from a body cavity can be completed within a short interval of time. The same applies for introduction of a calculus into the internal space of the properly inserted and positioned receptacle 1. Such manipulation of the receptacle and of a calculus at the inlet 3 can be monitored by an ultrasonic or X-ray apparatus. The person in charge manipulates the introducing means (such as the cable 14 or the conduits 4, 6, 7 or 4, 6, 7 and 12) to ensure that the partly or fully expanded receptacle 1 slides over and around the calculus so that the latter can be sealingly confined in the internal space of the receptacle as soon as the closure 5 is actuated to assume its closed or sealing position.

The improved apparatus is susceptible of numerous additional modifications without departing from the spirit of the invention. For example, the closure or sealing element 5 can constitute an inflatable and deflatable balloon which can be inflated by way of the conduit 4 or by resorting to a separate hollow flexible catheter, not shown. For example, the medium which is used to inflate the closure 5 can be atmospheric air. Each of the conduits 4, 6, 7 and 12 can constitute a hollow catheter.

It is advisable to employ a solvent which ensures complete dissolution of a calculus. This eliminates the danger of clogging the conduit 7 with particles of a calculus which would prevent rapid and predictable evacuation of solvent and calculus from the internal space of the receptacle 1.

A further important advantage of the improved apparatus is that it is not necessary to raise the pressure in the receptacle 1 to a relatively high level. In fact, the only rise of pressure which is necessary is that which ensures adequate expansion of an expandible or collapsible receptacle and/or adequate sealing action of an inflatable closure 5. The admission of solvent into and evacuation of solvent and of dissolved calculus from the receptacle 1 can take place during successive stages of treatment so that the pressure in the internal space of the receptacle (i.e., in the space which receives a calculus) rises very little or not at all. The same holds true when the pumps 8 and 9 are replaced with the vessels 108 and 109 of FIG. 6. The vessel 108 can be placed above the body of the patient and the vessel 109 is then placed to a level sufficiently below the level of the vessel 108 to ensure that the solvent can flow through the receptacle 1 without any, or without any appreciable, rise of pressure in the space for the confined calculus.

The means for flushing the receptacle 1 upon completed dissolution of a calculus therein can include a neutral liquid or a suitable buffering solution. Such flushing renders it possible to open the inlet 3 of the receptacle 1 prior to extraction of the apparatus from the body of a patient. The solvent can be an acid or an alkaline solution. The exact composition of the solvent will be selected in dependency on the composition of the calculus and/or upon the size of the calculus.

The utilization of an expandible and contractible (e.g., twistable) receptacle 1 constitutes an optional but highly desirable feature of the improved apparatus. Such collapsible receptacle can be utilized with advantage for removal of renal calculi. Thus, the receptacle will be collapsed to permit rapid and convenient passage through the urethra, through the urinary bladder and thereupon through an ureter, and the receptacle is thereupon expanded (either entirely or in part) prior to or after introduction into the pelvis of a kidney to permit convenient introduction of a calculus through the exposed inlet 3. Twisting of a receptacle 1 in a manner as shown in FIG. 3 is particularly simple and advantageous when the wall or walls of the receptacle are very thin so that the latter can be collapsed into a slender elongated member having a surprisingly small diameter. Untwisting of the receptacle can be effected by resorting to an expanding operation, e.g., with the pump 11 and conduit 12 of FIG. 4. In other words, it is possible to combine mechanical and pneumatic or hydraulic collapsing actions to ensure the deformation of the receptacle into a member adapted to be rapidly and painlessly introduced into a body cavity close to a calculus which is to be removed by dissolving it in a suitable liquid.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for removing soluble calculi from cavities of animal bodies, comprising a solvent-resistant receptacle having an inlet for admission of a calculus; means for introducing said receptacle into a calculus-containing cavity to thus admit a calculus into the introduced receptacle through said inlet; means for sealing said inlet upon admission of a calculus into the introduced receptacle; means for actuating said sealing means from the outside of the cavity; and means for circulating a solvent through the receptacle while the inlet is sealed and a calculus is confined in the receptacle to dissolve the confined calculus from said receptacle, said sealing means comprising an inflatable and deflatable closure for said inlet.

2. The apparatus of claim 1, wherein said receptacle comprises a collapsible and expandible sac.

3. The apparatus of claim 1, wherein said circulating means comprises means for admitting a solvent into the receptacle from the exterior of the cavity and means for evacuating the solvent and the dissolved calculus from the receptacle to the exterior of the cavity.

4. The apparatus of claim 3, wherein said admitting means comprises a first conduit and said circulating means further comprises means for forcing solvent into said conduit at the exterior of the cavity, said evacuating means comprising a second conduit and said circulating means further comprising means for receiving liquid solvent and dissolved calculus from said receptacle to the exterior of the cavity.

5. The apparatus of claim 4, wherein at least one of said forcing and receiving means comprises a pump.

6. The apparatus of claim 4, wherein said forcing means comprises a solvent-containing first vessel disposed at a first level and said receiving means comprises a second vessel disposed at a second level below said first level.

7. The apparatus of claim 1, wherein said actuating means includes means for inflating said closure.

8. The apparatus of claim 7, wherein said inflating means comprises a conduit connected with said closure and extending from the cavity upon introduction of said receptacle, and means for forcing a fluid into said closure through said conduit from the exterior of the cavity.

9. The apparatus of claim 1, wherein said receptacle is deformable and further comprising means for deforming said receptacle from the exterior of a cavity upon introduction of the receptacle into such cavity.

10. The apparatus of claim 9, wherein said receptacle has a variable diameter.

11. The apparatus of claim 1, wherein said receptacle is collapsible to facilitate the introduction thereof into a cavity.

12. The apparatus of claim 11, wherein said receptacle includes a tubular member having a variable diameter.

13. The apparatus of claim 1, wherein said circulating means comprises at least one conduit extending from the introduced receptacle to the exterior of the cavity and at least one pump connectable with the at least one conduit at the exterior of the cavity receiving said receptacle.

14. The apparatus of claim 1, wherein said circulating means comprises at least one first conduit and said actuating means comprises at least one second conduit, said conduits forming part of a cable.

15. The apparatus of claim 1, wherein said circulating means comprises a plurality of conduits forming part of a cable.

16. The apparatus of claim 1, wherein said circulating means includes a plurality of conduits and said actuating means comprises at least one additional conduit, said conduits and said additional conduit together forming part of a single cable.

17. The apparatus of claim 1, wherein said receptacle is expandible and collapsible and further comprising means for expanding and collapsing said receptacle including at least one first conduit, said circulating means comprising at least one second conduit and said conduits forming part of a cable.

* * * * *